US007937131B2

(12) United States Patent
Cho et al.

(10) Patent No.: US 7,937,131 B2
(45) Date of Patent: May 3, 2011

(54) PET—MRI HYBRID APPARATUS AND METHOD OF IMPLEMENTING THE SAME

(75) Inventors: Zang Hee Cho, Seoul (KR); Young Bo Kim, Yongin-si (KR); Cheol Ok Lee, Incheon (KR)

(73) Assignee: Gachon University of Medicine & Science Industry-Academic Cooperation Foundation, Incheon (KR)

( * ) Notice: Subject to any disclaimer, the term of this patent is extended or adjusted under 35 U.S.C. 154(b) by 545 days.

(21) Appl. No.: 11/027,599

(22) Filed: Dec. 28, 2004

(65) Prior Publication Data

US 2006/0052685 A1 Mar. 9, 2006

(30) Foreign Application Priority Data

Sep. 6, 2004 (KR) .................. 10-2004-0070693

(51) Int. Cl.
*A61B 5/05* (2006.01)
(52) U.S. Cl. .............. 600/415; 600/407; 5/601; 5/613; 52/111
(58) Field of Classification Search ........... 600/407–480
See application file for complete search history.

(56) References Cited

U.S. PATENT DOCUMENTS

| | | | | |
|---|---|---|---|---|
| 5,851,182 | A | * | 12/1998 | Sahadevan ................. 600/407 |
| 6,205,347 | B1 | | 3/2001 | Morgan et al. |
| 6,470,207 | B1 | * | 10/2002 | Simon et al. ................. 600/426 |
| 6,603,991 | B1 | * | 8/2003 | Karmalawy et al. ......... 600/411 |
| 6,631,284 | B2 | * | 10/2003 | Nutt et al. ..................... 600/427 |
| 6,697,660 | B1 | * | 2/2004 | Robinson ..................... 600/409 |

(Continued)

FOREIGN PATENT DOCUMENTS

| DE | 10012152 A1 | 9/2000 |
|---|---|---|
| WO | WO 03/032838 A2 | 4/2003 |

(Continued)

OTHER PUBLICATIONS

Raylman et al, "Combined MRI-PET Scanner: A Monte Carlo Evaluation of the Improvements in PET Resolution Due to the Effects of a Static Homogenous Magnetic Field", Aug. 1996, IEEE Transactions on Nuclear Science, vol. 43, No. 4, pp. 2406-2412.*

(Continued)

*Primary Examiner* — Brian Casler
*Assistant Examiner* — Nasir Shahrestani
(74) *Attorney, Agent, or Firm* — Patterson Thuente Christensen Pedersen, P.A.

(57) ABSTRACT

There is provided a PET-MRI hybrid apparatus and method for integrating a PET image and an MRI image so that anatomical, hemodynamical and molecular information on human tissues are simultaneously presented in a single image. The PET-MRI hybrid system comprises a first scanner for obtaining anatomical and hemodynamical information, and a second scanner for obtaining molecular and functional information on the human tissues. Along a path between the first scanner and the second scanner, a transferring railway system which includes runs, and a movable bed for supporting a subject installed on the railway. The PET-MRI hybrid system also comprises a "RF+ magnetic" shield and a "magnetic" shield between path between the first scanner and the second scanner, which switch between an open status and a close status in a completely synchronized manner to assure a complete magnetic shield for the PET system at any given time. The subject is fastened on the bed and transferred along the railway between the first and second scanner to provide accurately fused MRI and PET images.

12 Claims, 11 Drawing Sheets

U.S. PATENT DOCUMENTS

| | | | |
|---|---|---|---|
| 7,075,087 B2* | 7/2006 | Wang et al. | 250/363.04 |
| 7,190,991 B2* | 3/2007 | Cable et al. | 600/407 |
| 2004/0002641 A1* | 1/2004 | Sjogren et al. | 600/407 |
| 2004/0045155 A1* | 3/2004 | Tsuda | 29/607 |
| 2004/0097805 A1* | 5/2004 | Verard et al. | 600/428 |
| 2004/0162457 A1* | 8/2004 | Maggiore et al. | 600/1 |
| 2005/0080333 A1* | 4/2005 | Piron et al. | 600/417 |
| 2005/0206967 A1* | 9/2005 | Viswanth et al. | 358/474 |
| 2005/0245817 A1* | 11/2005 | Clayton et al. | 600/424 |
| 2006/0025669 A1* | 2/2006 | Ramamurthy et al. | 600/407 |
| 2006/0036153 A1* | 2/2006 | Laken | 600/410 |

FOREIGN PATENT DOCUMENTS

WO    WO 2005/005381 A3    1/2005

OTHER PUBLICATIONS

Vogl, et al., "Hybrid MR interventional imaging system: combined MR and Angiography suites with single interactive table. Feasibility study in vascular Liver tumor procesures," *Eur Radiol*, vol. 12, pp. 1394-1400 (2002).

Office Action cited in German Counterpart Application Issued May 19, 2010, 9 Pgs.

* cited by examiner

UHF MRI​        HRRT PET

PET—MRI HYBRID APPARATUS AND METHOD OF IMPLEMENTING THE SAME

FIELD OF THE INVENTION

The present invention generally relates to an apparatus and method for non-invasively obtaining an image featuring information on internal human tissues, and more particularly to an apparatus and method for integrating positron emission tomography (PET) and magnetic resonance imaging (MRI) to provide a single high spatial resolution image which features anatomical information, as well as molecular and functional information on the internal human tissues.

BACKGROUND OF THE INVENTION

PET was first developed in 1975 by two different groups of scientists. The first group is comprised of Dr. Zang-Hee Cho, et al. at University of California at Los Angeles (UCLA), while the second group is composed of Dr. M. Ter-Pogossian and Dr. M. Phelps, et al. at Washington University, St. Louis, Mo. Since then, PET has been further developed and innovated by several different commercial companies, including CPS-CTI. PET has been the only machine capable of performing molecular and functional imaging both on the body and the brain until 1992 (Although fMRI appeared in 1992, it was limited to the brain and the hemodynamics).

MRI, on the other hand, has been developed in 1973 by Dr. P. Lauterbur. It is somewhat similar to CT or PET, but is different in terms of physical principle. Over 10,000 MRI units are now in use at various hospitals throughout the world. MRI is essentially a morphological or anatomical imaging tool rather than functional, and thus lacks molecular specificity. However, MRI has much higher temporal and anatomical resolutions than PET. In 1992, a functional imaging capability has been incorporated into MRI by Dr. S. Ogawa, hence resulting in the creation of fMRI. By incorporating the use of such additional capability, fMRI became one of the most powerful brain imaging tools in the field of neuroscience.

When the fMRI was first introduced into the world, it was so impressive in brain imaging that the entire neuroscience community embraced this new device with great enthusiasm. The fMRI had indeed changed the landscape of neuroscience research. This excitement was short lived, however, as the demands for molecular specificity arose, which essentially renewed the interest in PET. As is well known in the art, PET has two major functional capabilities, namely, the functional capabilities for measuring metabolism of certain substrates such as glucose and ganciclovir and affinity/distributions of specific neuro-receptors for a certain ligand (i.e., molecular specificity and sensitivity). Theses capabilities are generally lacking in fMRI or MRI.

As explained above, PET and MRI are characterized by their own advantages and disadvantages. More specifically, PET is capable of providing molecular and functional information on human tissues with exceptionally high contrast. However, PET is limited in providing accurate anatomical information since it has inherently lower spatial resolution. Contrary to PET, however, MRI is capable of providing detailed anatomical information on human tissues, but cannot provide molecular and functional information.

Figure 1:
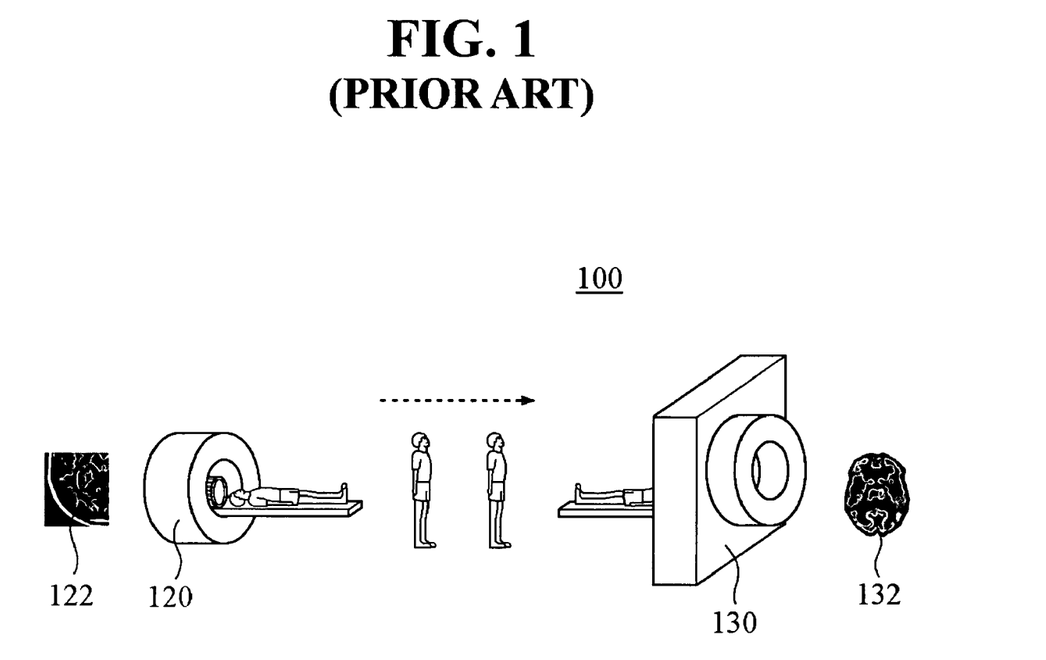
FIG. 1 shows a schematic diagram illustrating a conventional system in the art.

Due to the foregoing pros and cons of PET and MRI, there have been many attempts in the art to integrate them together. However, none of the prior attempts achieved any practical success. For example, FIG. 1 shows a prior attempt for integrating conventional MRI (using 1.5-3.0T magnetic field) and PET (or PET/CT (Computer Tomography)). More specifically, a conventional system 100 is comprised of an MRI device 120 and a PET/CT device 130. As is well known in the art, the MRI device 120 measures atomic, chemical and physical aspects of a given tissue by using magnetic properties of subject materials that are present in the human body. As shown in FIG. 1, the MRI device 120 manipulates the measurements in order to produce an MRI image 122, which include anatomical information on human tissues. As is further well known in the art, the PET/CT 130 detects gamma rays (i.e., the 511 kev annihilation photons), which are used to produce a PET image 132 representing molecular and functional information on human tissues. The gamma rays originate from a biological sample that is marked by a positron-emitting radionuclide, such as F18, and are introduced into the human body. When a positron is emitted from the radionuclide and encounters an electron in the body, a pair of gamma rays is generated.

In such conventional system, the MRI device 120 and the PET/CT device 130 are totally separated from each other. They are placed distantly apart from each other and located in different spaces. The reason why the MRI device 120 and the PET/CT device 130 cannot be placed in close proximity of each other is due to the strong magnetic field generated by the MRI device 120, which can damage the PET/CT device 130. In particular, a photomultiplier used in the PET/CT device 130 is very sensitive to even a small external magnetic field. Therefore, the PET/CT device 130 cannot normally operate when the MRI device 120 is located in close proximity thereto.

In the conventional system, a patient has to be frequently transported in and out. This is because the patient has to be moved from a place, which is installed with the MRI device 120, to a different place where the PET/CT device 130 is located. A PET imaging is usually taken after an MRI imaging. However, an MRI imaging may precede a PET imaging. Therefore, even if the MRI and PET images are obtained, it is very difficult to combine them with a precision that is needed in image fusion. This is due to the physical separation between the MRI device 120 and the PET/CT device 130, especially when the desired resolution is high. Thus, there is a difficulty in combining a molecular image from the PET device 130 with an anatomical image from the MRI device 120, with an arrangement as shown, that is, when they are separated.

In addition, because the two images (i.e., one from MRI and the other from PET) are taken at different places (different environments or conditions) and times (metabolic changes will occur between them), it is highly possible that the conditions between such times and places may change and thus inconsistency is likely to be introduced. In other words, it is generally not suitable to combine an anatomical image from the MRI device 120 (or an oxygen consumption or hemodynamic image from fMRI) with a molecular image from the PET/CT device 130 in a conventional setting, especially in brain imaging due to the fine details of the brain structures.

Accordingly, there is a need for a system capable of providing a medical image that is truly integrated and contains both the anatomical information and molecular information within a time frame that is suitable for brain's functional changes or dynamics.

SUMMARY OF THE INVENTION

Therefore, the primary object of the present invention is to provide a PET-MRI hybrid apparatus (i.e., a PET and MRI integrated system) and a method of implementing the same so that molecular and anatomical information on human tissues can be simultaneously obtained in a single image (Hardware part).

Another object of the present invention is to provide a set of software for performing mathematical and computer techniques to integrate an MRI image and a PET image in order to provide a high spatial resolution molecular image.

In accordance with an embodiment of the present invention, the present invention is directed to an apparatus for providing anatomical information, as well as molecular and functional information, of a subject. Such apparatus comprises: a first scanner for obtaining said hemodynamical and anatomical information; a second scanner for obtaining said molecular and functional information; and an RF shield capable of switching between an open status and a close status, and for further sheltering a predetermined space including said first scanner from external RF fields in said close status. A transferring railway is provided which runs along a path from said first scanner via said RF shield to said second scanner. A bed is also provided to move and support said subject along said transferring railway.

In accordance with another embodiment of the present invention, there is provided an imaging apparatus for providing anatomical information, as well as molecular and functional information, of a subject. The apparatus comprises: a first scanner for obtaining said anatomical information, as well as functional information on said subject; a second scanner for obtaining said molecular and functional information; a RF+ magnetic shield for sheltering a space including said first scanner from external RF fields, and for further preventing magnetic fields of said first scanner from leaking outside; a magnetic shield for sheltering a space including said second scanner from said magnetic fields out of said first scanner; a transferring railway running along a line from said first scanner via said RF+ magnetic shield and said magnetic shield to said second scanner; and a bed movable along said transferring railway and for supporting said subject.

In accordance with still another embodiment of the present invention, there is provided a method of providing anatomical information, as well as molecular and functional information, of a subject. Such method comprises the steps of: transferring said subject to a space where said anatomical information is obtained, sheltering from external RF fields said space where said anatomical information is obtained; obtaining said anatomical information; transferring said subject to a space where said molecular and functional information can be obtained; and obtaining said molecular and functional information.

In accordance with still yet another embodiment of the present invention, there is provided a method of providing anatomical information, as well as molecular and functional information, of a subject. Such method comprises the steps of: transferring said subject to a first space where said anatomical information is obtained, sheltering from external RF fields said first space where said anatomical information is obtained; obtaining said anatomical information; transferring said subject to a second space where said molecular and functional information can be obtained; sheltering from external magnetic fields said second space where said molecular and functional information is obtained; and obtaining said molecular and functional information, in a totally synchronized manner so that at an any given time, said second space is not exposed to magnetic fields from said first space.

BRIEF DESCRIPTION OF DRAWINGS

The above object and features of the present invention will become more apparent from the following description of the preferred embodiments given in conjunction with the accompanying drawings.

DETAILED DESCRIPTION OF THE PRESENT INVENTION

1. An Embodiment of the Low Field MRI+PET/CT Hybrid System

Figure 2:
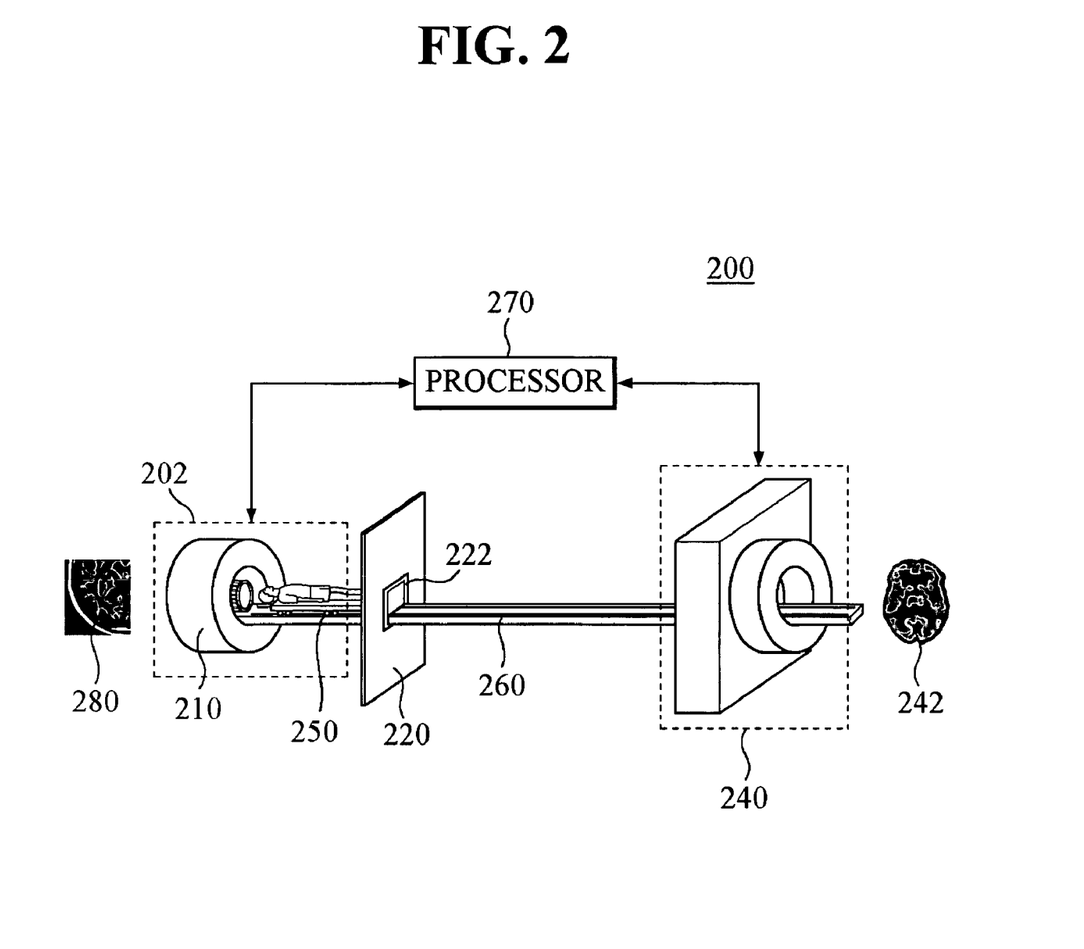
FIG. 2 shows a schematic diagram of a first embodiment of a low field MRI+PET/CT hybrid system in accordance with the present invention.

In FIG. 2, there is provided an embodiment of the low field MRI+PET/CT hybrid system. In the embodiment of FIG. 2, a system 200 generally comprises an MRI scanner 210, a radio field (RF) shield 220, a PET/CT scanner 240, a patient bed 250, a transferring railway 260, and an imaging processor 270.

As is well known in the art, the MRI scanner 210 provides anatomical and structural information as well as functional imaging on human tissues by using magnetic fields of 1.5-3.0T. The MRI scanner 210 is self-shielded so as to prevent the magnetic fields from leaking out of the scanner when in use.

The RF shield 220 protects the MRI block 202 from being adversely affected by external RF field. In the MRI block 202, electrical stimuli are applied to nuclei in the human tissues in order to place the nuclei in an excitation status. When the nuclei in the excitation status return to de-excitation status, they emit high frequency RF signals. The MRI scanner 210 receives the RF signals emitted from the nuclei by an RF coil to reconstruct anatomical information on the human tissues. The RF signals, which are generated when the status of the nuclei changes from excitation to de-excitation, are overlapped in a frequency range with those used in an ordinary radiobroadcast or communication system. Unless the MRI block 202 is sheltered from that of the external RF signals, the MRI block 202 cannot tell RF signals from the human tissues from that of the external RF signals, and thus fails to correctly obtain anatomical information. Therefore, the RF shield 220 shelters the MRI block 202 from the external RF signals to avoid such a problem.

The PET/CT scanner 240 is able to obtain data about internal human tissues using X-rays together with positron-emitting radionuclide. Thus, both anatomical and molecular imaging can be obtained. It should be noted herein that the PET/CT scanner 240 was recently developed.

The patient bed 250 supports and moves a patient back and forth between the MRI scanner 210 and the PET/CT scanner 240. The patient bed 250 also locates a patient to a RF coil of the MRI scanner 210.

The transferring railway 260 extends between the MRI scanner 210 and the PET/CT scanner 240. The railway 260 is required to maintain a prescribed relationship between image-taking origins for the MRI scanner 210 and the PET/CT scanner 240 when the patient is transferred along the railway between the scanners. However, it is important that the railway 260 performs the above task comfortably with minimal positional and psychological disturbances.

The imaging processor 270 performs the necessary algorithms for generating both the MRI and PET images, such as the Fourier transformation and three-dimensional reconstruction. The algorithms can also be directed to other mathematical transformations such as geometrical error calibration and correction in combining MRI and PET images.

Figure 3:
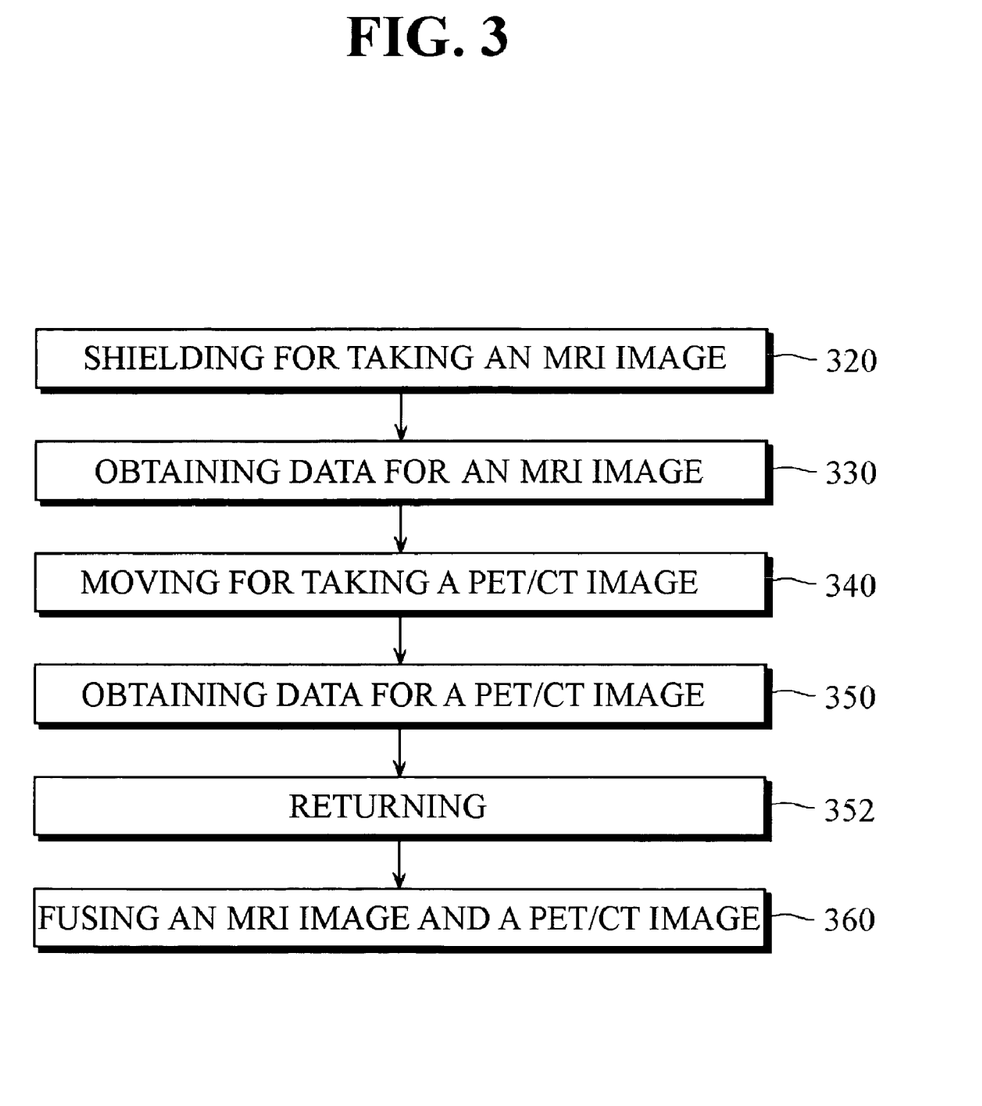
FIG. 3 is a flowchart illustrating the operation of a first embodiment of a low field MRI+PET/CT hybrid system in accordance with the present invention.

FIG. 3 illustrates a method performed in the first embodiment in accordance with the present invention. In step 320, the method of the first embodiment starts by shielding the MRI block 202 when taking an MRI image. In this step, a patient is fixed on the patient bed 250. Then, the patient bed 250 moves along the transferring railway 260 toward the MRI scanner 210. When the patient bed 250 reaches a predetermined distance prior to the RF shield 220, a shutter 222 equipped thereon starts to open. After the patient's feet pass through the shutter 222, the shutter 222 then closes. The patient bed 250 continues to move toward the MRI scanner 210 until the patient's head becomes located inside the RF coil.

In step 330, the MRI scanner 210 applies RF fields and gradients to the patient's head, from where the anatomical information is obtained, and emits RF pulse signals. Generally, each of nuclei, of which human tissues are composed, has its own Larmor frequency when it is placed in a given magnetic field. Thus, the patient's tissues, where the RF pulse signals are applied, emit magnetic resonance (MR) signals corresponding to the Larmor frequency. The MR signals are collected by the RF coil of the MRI scanner 210 and are transmitted to the imaging processor 270. The imaging processor 270 performs a signal processing, such as the Fourier transformation, on the MR signals to generate an MRI image 280. The method for collecting and processing the MR signals for the MRI image will not be explained herein in detail since such method does not have a direct relationship with the invention.

In step 340, the patient bed 250 moves along the transferring railway 260 toward the PET/CT scanner 240 in order to take a PET/CT image. As explained above, when the patient bed 250 reaches a predetermined distance prior to the RF shield 220, a shutter 222 equipped thereon starts to open. After the patient bed 250 goes through the shutter 222, it closes.

In step 350, the patient bed 250 arrives within the PET/CT scanner 240. The PET/CT scanner 240 starts to detect gamma rays (annihilation photons) from the same patient's parts as the MRI scanner 210 examined.

The gamma rays are originated from a biological probe that is a substrate, such as glucose marked by a positron-emitting radionuclide and is introduced via an intravenous injection into a human body. More specifically, the radionuclide decays by emitting a positron and neutron, and the emitted positron collides with an electron in the human tissues. The collision causes an annihilation of the positron and electron to generate a pair of gamma rays. In the annihilation process, a pair of gamma (annihilation photons) rays is generated in 180 degree opposite directions since the momentum must be conserved. Due to this property of the annihilation, detectors of the PET/CT scanner 240 are arranged to form a circle such that a pair of detectors in the opposite direction simultaneously receives a set of gamma rays, 511 kev photons. This reception means that there was a collision of a positron and an electron somewhere along the line extending between the two receiving detectors, which is called a coincidence line. A plurality of coincidence lines is obtained in the PET/CT scanner 240 to form a tomographic image, through mathematical reconstruction at a process 270.

The PET/CT scanner 240 transmits the coincidence data to the imaging processor 270. Then sufficient number of coincidence lines is obtained, the imaging processor 270 performs signal processing such as filtered backprojection and correction of gamma ray attenuation for the final image reconstruction of a PET image 242. The method for processing the coincidence data for PET images will not be explained herein in detail since such method does not have a direct relationship with the invention.

Next, in step 352, the patient bed 250 moves backward along the transferring railway 260 to the mid point between the MRI scanner 210 and PET/CT scanner 240. The patient is withdrawn at this position when the patient bed 250 stops at the middle of the MRI scanner 210, and the PET/CT scanner 240.

In step 360, the imaging processor 270 generates two images (i.e., the MRI image 280 and the PET image 242) and fuses together and obtains a fused image of anatomical MRI image 210 and the PET/CT image 240. In order to fuse the MRI and PET images as correctly as possible, the transferring railway 260 is rigidly and accurately maintained to meet the desired geometrical and mechanical accuracy. To further assist fusion accuracy, a laser-guided calibrating device is also equipped in both the MRI scanner 210 and the PET/CT scanner 240. Finally, the imaging processor 270 produces a fusion image on a display apparatus (not shown), thereby providing a medical image that contains anatomical, hemodynamical, molecular and functional information, which are truly synchronized in terms of time and space.

2. An Embodiment of the Brain Dedicated UHF-MRI+HRRT-PET Hybrid System

Figure 4A:
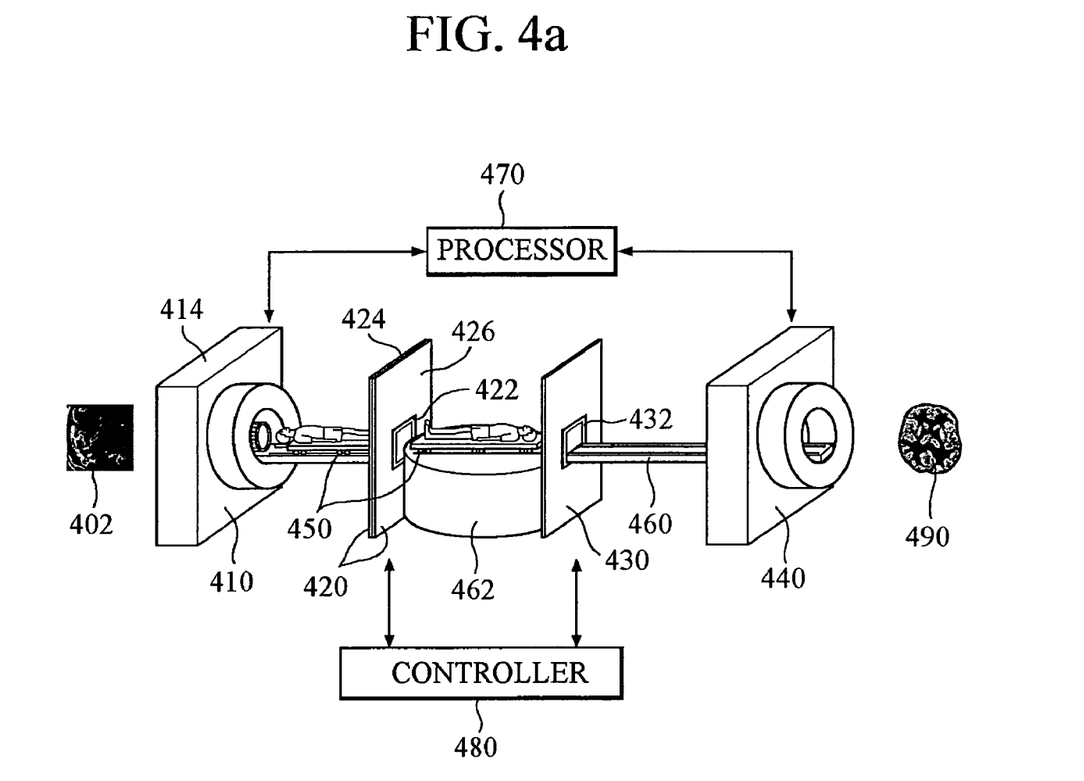
FIG. 4(a) shows a schematic diagram of a second embodiment of an ultra high field (UHF) MRI+High Resolution Research Tomography (HRRT) PET hybrid system in accordance with the present invention.

FIG. 4(*a*) shows an embodiment of the brain dedicated UHF-MRI+HRRT-PET hybrid system. As illustrated in FIG. 4(*a*), a system 400 comprises a brain dedicated MRI scanner 410, a RF+ magnetic shield 420 for MRI, a magnetic shield 430 for HRRT-PET, a HRRT-PET scanner 440, a patient bed 450, a transferring railway 460, a controller 480 for synchronously controlling the RF+ magnetic shield 420 and a magnetic shield 430, and an imaging processor 470.

The UHF-MRI scanner 410 provides anatomical, structural as well as functional information on a brain by using ultra-high magnetic fields over 7.0T. Using the ultra-high magnetic field, the UHF-MRI scanner 410 can construct a medical image showing even cortical laminae of a brain. However, the unusually high magnetic fields of the UHF- MRI scanner 410 may influence even at a longer distance. Thus, a specialized shield is required to completely shield the magnetic fields (e.g., stray fields), especially when a device vulnerable to the magnetic fields, such as the PET scanner, is placed in close proximity.

In this embodiment, the RF+ magnetic shield 420 for MRI prevents the high magnetic field of the UHF-MRI scanner 410 from leaking outside. In addition, the magnetic shield 430 further protects PET scanner (HRRT-PET) 440 against the stray magnetic fields of the UHF-MRI scanner 410. In the present embodiment, these two shields 420 and 430 are synchronously controlled to completely shield the magnetic field of the UHF-MRI scanner 410 by the controller 480. With these double magnetic field shields, the HRRT-PET scanner 440, which is extremely sensitive to a magnetic field, can safely be placed sufficiently close to the UHF-MRI scanner 410.

In the present embodiment, in addition to preventing the magnetic fields of the UHF-MRI scanner 410 from leaking, the RF+ magnetic shield 420 also stops external RF fields from being introduced to the UHF-MRI scanner 410. With respect to stopping RF fields, the RF+ magnetic shield 420 also comprises a high frequency RF shield 426.

Figure 5A:
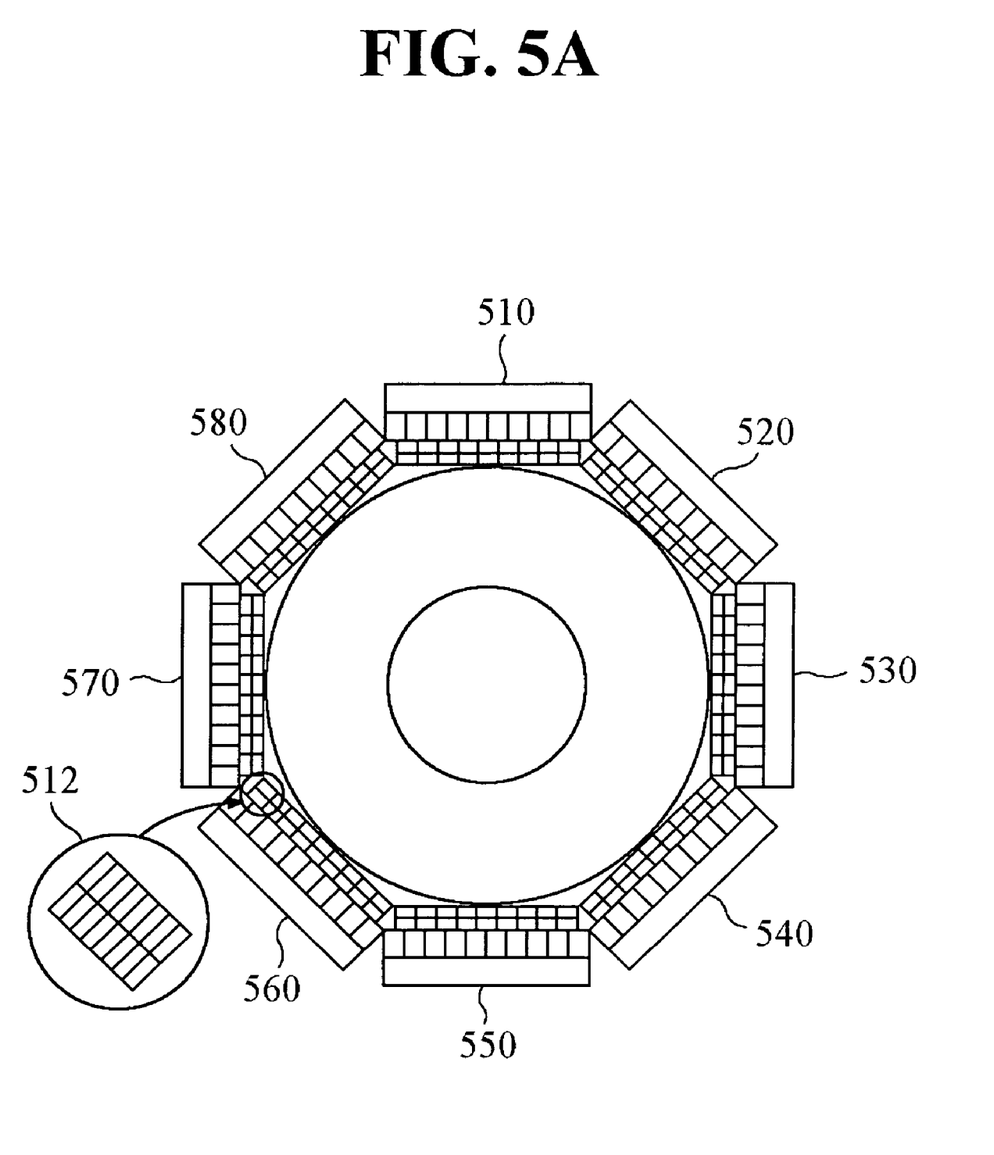
FIG. 5(a) shows a simplified structure of a HRRT PET scanner used in a second embodiment of a UHF MRI+HRRT PET hybrid system in accordance with the present invention.
Figure 5B:
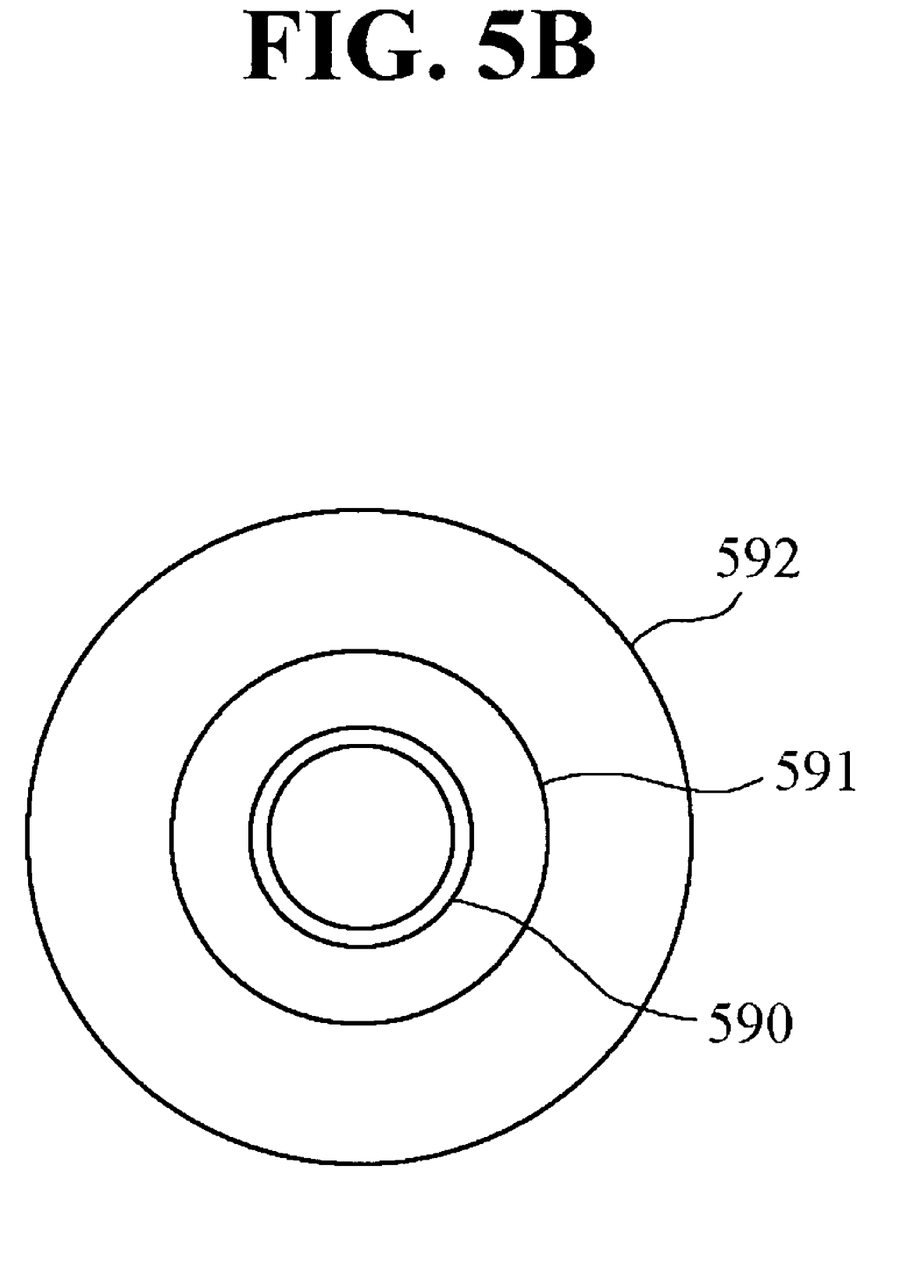
FIG. 5(b) shows an UHF-MRI entrance sketch in a second embodiment of a UHF MRI+HRRT PET hybrid system in accordance with the present invention.

As illustrated in FIG. 5A, the recently developed HRRT-PET scanner 440 has a total of 59,904×2 detectors and 1,200 PMTs. More specifically, the HRRT-PET scanner 440 includes 8 batches of detectors 510-580, wherein each batch is comprised of 9×13 blocks 512. In FIG. 5B, an entrance sketch of UHF-MRI (7.0T) is shown. In this illustration, an element 590 is a head-only RF coil for maximization of head imaging. Further in the illustration, an element 591 is a gradient ($w_i$) designed for a brain, while an element 592 is the magnet (7.0T).

The patient bed 460 supports and moves a patient back and forth between the UHF-MRI scanner 410 and the HRRT-PET scanner 440. It can locate a patient to a RF coil of the UHF-MRI scanner 410, like the bed 250 of the first embodiment.

The transferring railway 460 runs between the UHF-MRI scanner 410 and the HRRT-PET scanner 440. The railway 460 is desirably required to maintain a prescribed relationship between image-taking origins for the UHF-MRI scanner 410 and the HRRT-PET scanner 440 when the patient is transferred along the railway between the scanners.

The transferring railway 460 further comprises a rotary table 462 to rotate a patient by 180 degrees, which is installed between the RF+ magnetic shield 420 and the magnetic shield 430. After being out of the UHF-MRI scanner 410, the rotary table 462 makes it easy for a patient's head to enter the HRRT-PET scanner 440, whose bore is too small to pass a patient's trunk.

The imaging processor 470 performs the necessary algorithms for generating both the MRI and PET images, such as the Fourier transformation and three-dimensional reconstruction. The algorithms can also be directed to other mathematical transformation and geometrical error correction in combining the MRI and PET image.

The controller 480 controls the RF+ magnetic shield 420 and the magnetic shield 430 in a synchronous manner such that the above-described high magnetic fields of the UHF-MRI scanner 410 do not reach the HRRT-PET scanner 440 at any given time. In more detail, the controller 480 controls movements of the patient bed 450 along the railway 460, and opening and closing of the RF+ magnetic shield 420 and the magnetic shield 430 based on the position of the patient bed 450 to absolutely prevent the magnetic fields of the UHF-MRI scanner 410 from leaking outside and reaching to the HRRT-PET scanner 440.

Figure 4B:
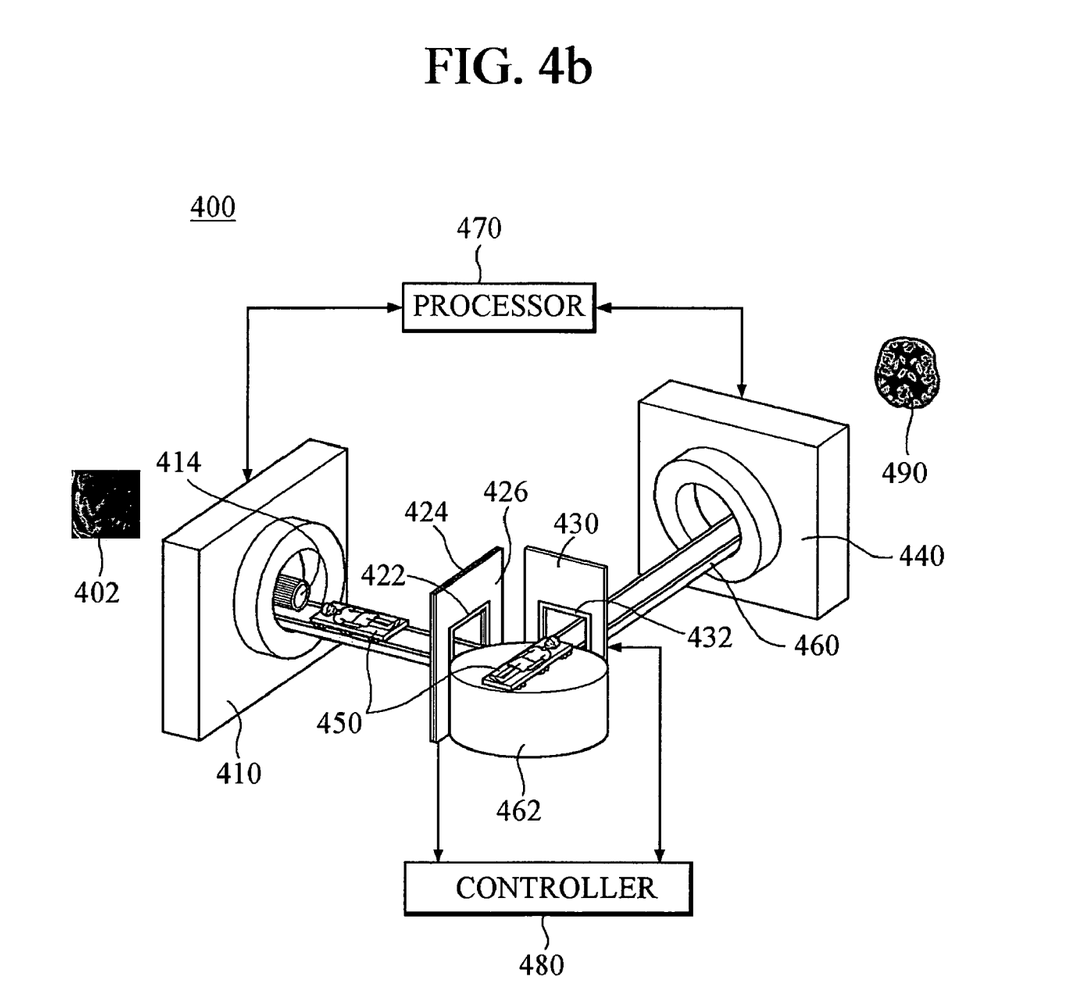
FIG. 4(b) shows a schematic diagram modifying second embodiment of an ultra high field (UHF) MRI+High Resolution Research Tomography (HRRT) PET hybrid system in accordance with the present invention.

FIG. 4(b) shows modification of second embodiment of the brain dedicated UHF-MRI+HRRT-PET hybrid system. This embodiment shown in FIG. 4(b) is identical to that in FIG. 4(a) except the transferring railway 460. As illustrated in FIG. 4(b), a portion of the transferring railway 460, which is placed upon the rotary table 462 in the embodiment of FIG. 4(b), can be turned at a right angle. Therefore, the patient is rotated 90 degrees by the rotary table 462 before the patient moves via the magnetic shield 430 toward the HRRT-PET scanner 440.

The above modification of the railway 460 contributes to the reduction of magnetic field on to the HRRT-PET scanner 440, which magnetic field is caused by the stray magnetic fields of the UHF-MRI scanner 410. In the embodiment in FIG. 4(b), the UHF-MRI and the HRRT-PET bores do not directly face one another. Consequently, the stray magnetic fields of the UHF-MRI scanner 410 is further reduced compared with the straight configuration of the one is FIG. 4(a). Consequently, it reduces further the stray magnetic field on to the HRRT-PET scanner 440.

Figure 6:
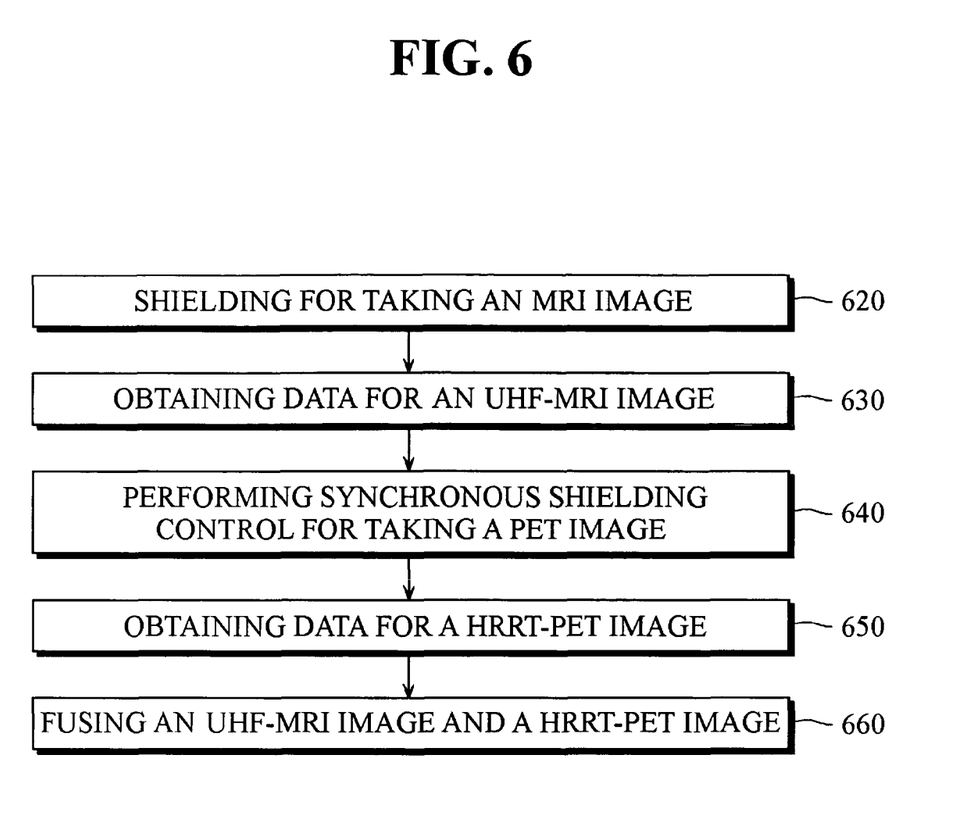
FIG. 6 is a flowchart illustrating the operation of a second embodiment of a UHF MRI+HRRT PET hybrid system in accordance with the present invention.

FIG. 6 illustrates a method performed in the second embodiment in accordance with the present invention.

In step 620, a patient is fixed on the patient bed 450. The patient bed 450 moves in a manner as to direct the head first along the railway 460 to transfer toward the UHF-MRI scanner 410. When the patient is moving, the RF+ magnetic shield 420 should be opened and the magnetic shield 430 should be closed. After the patient's feet pass through the shutter, the shutter then closes. The patient bed 450 continues to move toward the UHF-MRI scanner 410 until the patient's head is located inside an RF coil 414 of the UHF-MRI scanner 410.

In step 630, the UHF-MRI scanner 410 applies RF fields and gradients. The patient emits RF signals, which belong to the patient's head inserted within the RF coil 414. In general, the higher the magnetic fields are, the more larger and reliable and accurate information can be obtained. Thus, compared with the conventional MRI scanner, the UHF-MRI scanner 410 of 7.0T can provide a resolution much higher than the conventional system and provides even an image of cortical laminae of a brain. RF signals are emitted from the patient's brain tissues responsive to the RF pulses, and are collected by the RF coil 414 of the MRI scanner 410. They are then transmitted to the imaging processor 470. The imaging processor 470 performs a signal processing such as the Fourier transformation on the received signals to generate an UHF-MRI image 402. The method for processing the received RF signals for MRI images will not be explained herein in detail since such method does not have a direct relationship with the invention.

In step 640, the patient bed 450 starts moving along the transferring railway 460 from the UHF-MRI scanner 410 toward the RF+ magnetic shield 420 after all UHF-MRI image data collecting procedures for generating an MRI image are finished. When the patient's feet fixed on the patient bed 450 reaches a predetermined distance prior to the RF+ magnetic shield 420, a shutter 422 equipped thereon begins to open. After the patient's head on the patient bed 450 goes through and completely out of the RF+ magnetic shield 420, the shutter 422 closes. Then, the patient bed 450 is placed somewhere on the transferring railway 460 between the RF+ magnetic shield 420 and the magnetic shield 430.

At this point, it should be noted that the HRRT-PET scanner 440 can be adversely influenced by the magnetic fields leaked via the shutter 422 from the UHF-MRI scanner 410. Thus, it is important that the RF+ magnetic shield 420 and the magnetic shield 430 are controlled in a synchronous way such that both shields should never be in an open status at the same time at any given time. In other words, since the UHF-MRI scanner 410 utilizes high magnetic fields over 7.0 T, the shutter 422 (RF+magnetic shield also) equipped on the RF+ magnetic shield 420 must be closed after the patient bed 450 is out of the RF+ magnetic shield 420. Before the patient bed 450 reaches a predetermined distance from the shutter 432 (magnetic shield) equipped on the magnetic shield 430 starts to open.

Design is made so that before the patient bed 450 approaches the magnetic shield 430, the patient is rotated 180 degrees by the rotary table 462 to make it easy for the patient's head to enter the HRRT-PET scanner 440, whose bore is for the head only and therefore is small. Once the patient is rotated, the patient's head is placed toward the HRRT-PET scanner gantry 440 and moves toward the magnetic shield 430. When the patient bed 450 reaches a predetermined distance prior to the magnetic shield 430, the shutter 432 equipped thereon starts to open. After the patient bed 450 goes through the shutter 432, the shutter closes again to prevent the magnetically sensitive HRRT-PET scanner 440 from being influenced by the magnetic fields from the UHF-MRI. As described above, when the shutter 432 equipped on the magnetic shield 430 is in an open status, the shutter 422 equipped on the RF+ magnetic shield 420 must be in a close status.

Next, in step 650 of the present embodiments, the patient bed 450 arrives within the HRRT-PET scanner 440 to take an HRRT-PET image. The HRRT-PET scanner 440 detects gamma rays from the same areas of patient as the UHF-MRI scanner 410 examined. Compared to the conventional scanner, the HRRT-PET scanner 440 has much large number of detectors, therefore the more efficient in detecting gamma rays from the subject. In addition, the bore of the HRRT-PET scanner 440 is small to improve the detection efficiency. With these characteristics, the HRRT-PET scanner 440 can generate a PET image 490, whose spatial resolution and efficiency are much more superior than the existing PET scanners.

The HRRT-PET scanner 440 collects data from the patient and transmits them to the imaging processor 470. The method for processing the data for constructing PET images will not be explained herein in detail since such method does not have a direct relationship with the invention.

After the HRRT-PET scanner 440 obtains data sufficiently enough to construct a PET image, the patient bed 450 moves along the transferring railway 460 back to a point between the RF+ magnetic shield 420 and the magnetic shield 430 in order to conduct another examination.

Figure 7:
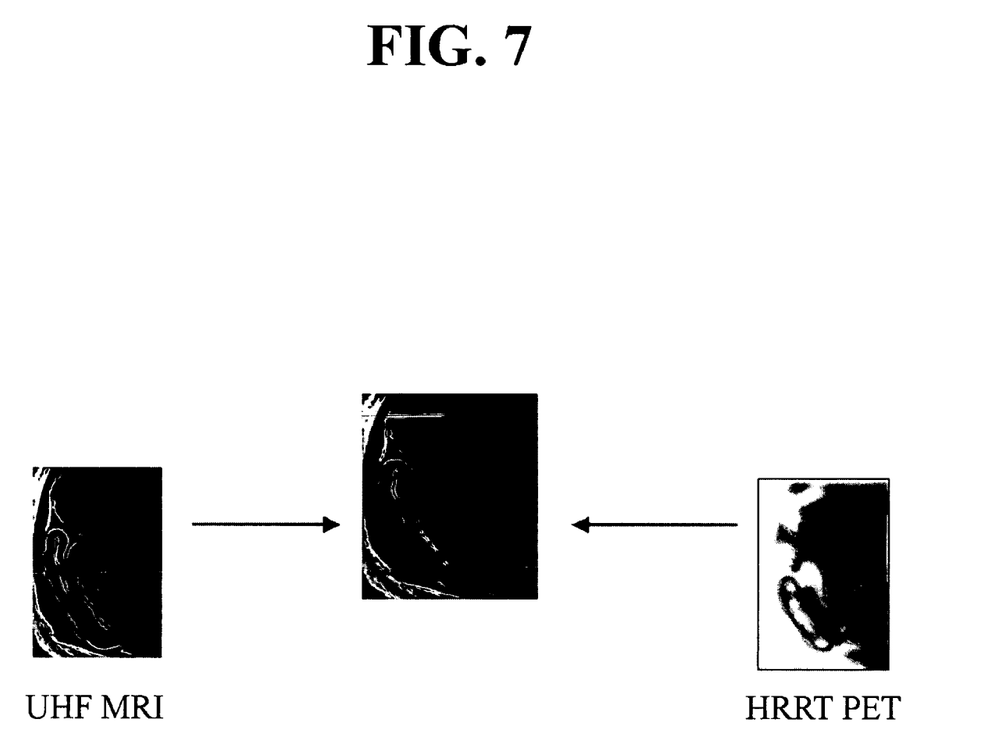
FIG. 7 shows a fusion image that the present invention generates.

In step 660, the imaging processor 470 fuses data obtained from the UHF-MRI scanner 410 and the HRRT-PET scanner 440 to construct a medical image wherein anatomical information and molecular information are synchronized in time and space. To further improve the image fusion, a laser-guided calibrating device is additionally used in both the UHF-MRI scanner 410 and the HRRT-PET scanner 440. FIG. 7 shows an example of a medical image wherein MRI and PET images are fused in accordance with the embodiment of the present invention.

The present embodiment of the invention provides a medical image wherein an UHF-MRI and HRRT-PET image data are fused to provide information (i.e., the identity of a molecular function of a specific human tissue) by accurately matching anatomical information with molecular information. As explained above, the present embodiment generates a medical image wherein anatomical, hemodynamical and molecular information are fused synchronously in terms of time and space. Therefore, all parameters of a neuroscience, which are necessary for medical treatment, cognitive science, emotion, learning and memory, and intelligence, among others, can be quantitatively measured by the present embodiment with a precision compatible to that of the 7.0T MRI image resolution. This achievement of the embodiment has been not possible by prior arts.

3. An Embodiment of the Micro PET+ Micro MRI Hybrid System

Figure 8:
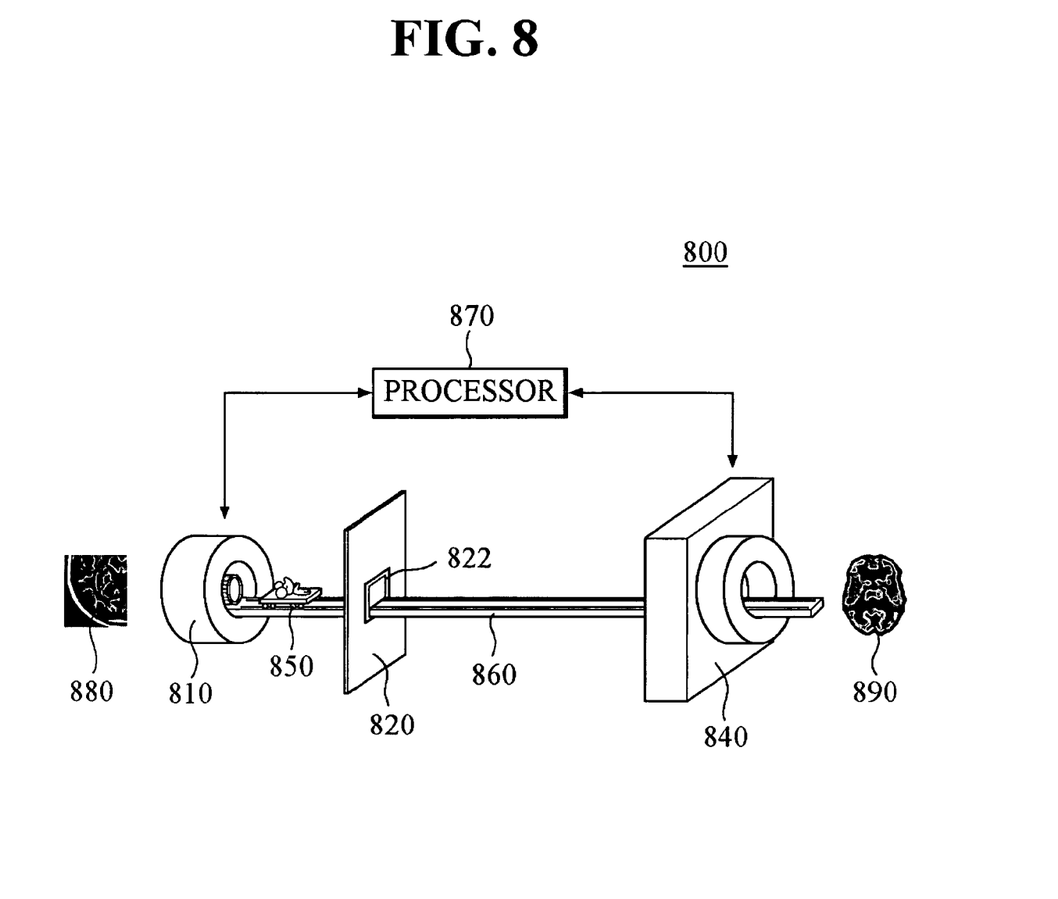
FIG. 8 shows a schematic diagram of a third embodiment of a micro MRI+micro PET hybrid system in accordance with the present invention.

Illustrated in FIG. 8 is an embodiment of the micro PET+ micro MRI hybrid system according to the present invention. A micro PET+ micro MRI hybrid system 800 comprises a micro MRI scanner 810, a RF shield 820, a micro PET scanner 840, a sample bed 850, a transferring railway 860, and an imaging processor 870.

The micro MRI scanner 810 of this embodiment is mainly used in research of animal models. The micro MRI scanner 810 provides anatomical information with same peripheral molecular information on an internal tissue of a sample. Although the micro MRI scanner 810 has a structure much similar to the MRI scanner for a human body, it uses a magnet of a smaller diameter and high magnetic fields (of about 7.0T-14.0T) micro MRI can increase its resolution up to 100 μm or less.

The micro PET scanner 840 is used mainly for the molecular imaging of animals. The micro PET scanner 840 also has a small diameter bore and can provide an image having a resolution close to 1 mm fwhm (full width half maximum).

In this embodiment, the RF shield 820 protects the micro MRI scanner 810 from being adversely affected by external RF fields or signals, as the RF shield 220 of the first embodiment of the low field MRI+PET/CT hybrid system.

The sample bed 850 fixes the sample to be inspected in order to have the sample unmovable during a scanning process by the micro MRI scanner 810 or the micro PET scanner 840.

The transferring railway 860 runs between the micro MRI scanner 810 and the micro PET scanner 840. The railway 860 is required to maintain a prescribed relationship between image-taking origins for the micro MRI scanner 810 and the micro PET scanner 840 when the sample is transferred along the railway between the scanners.

The imaging processor 870 is for generating a medical image of the sample by performing necessary computation, such as the Fourier transformation and three-dimensional reconstruction. The algorithms can also be directed to other mathematical and geometrical calibration for reconstructing the image.

Although the micro PET needs an RF and magnetic shield, it can be made relatively simple and inexpensive.

Figure 9:
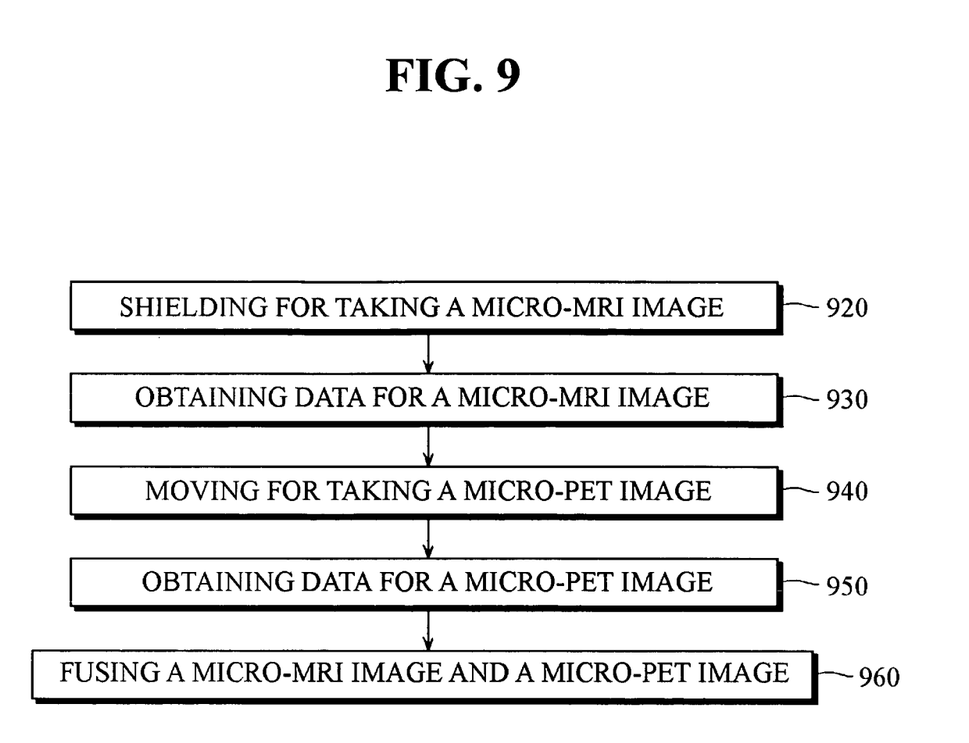
FIG. 9 is a flowchart illustrating the operation of a third embodiment of a micro MRI+micro PET hybrid system in accordance with the present invention.

FIG. 9 illustrates a method of the embodiment of a micro MRI+ micro PET hybrid system, which is similar to the method of the first embodiment of the low field MRI+PET/CT hybrid system.

First, in step 920, the method of this embodiment starts by shielding the micro MRI block during the imaging of the micro MRI. In this step, a sample is fixed on the sample bed 850. Then, the sample bed 850 moves along the transferring railway 860 toward the micro MRI scanner 810. After the completion of the micro MRI imaging, the sample will move toward RF shield 820. When the bed 850 reaches a predetermined distance prior to the RF shield 820, a shutter 822 (RF shield) equipped thereon starts to open. After the sample bed 850 goes through the shutter 822, the shutter 822 then closes.

In step 930, the micro MRI scanner 810 applies RF fields and gradients to the sample. In response to the RF pulse signals, the MR signals are generated from the sample and collected by the RF coil of the micro MRI scanner 810. The imaging processor 870 performs a signal processing such as the Fourier transformation on the MR signals to generate an MRI image 880. The method for collecting and processing the MR signals for an MRI image will not be explained herein in detail since such method does not have a direct relationship with the invention.

In step 940, the sample bed 850 moves along the transferring railway 860 toward the micro PET scanner 840. Then, the shutter 822 equipped on the RF shield 820 opens. Thereafter, the shutter 822 is closed completely when the patient bed 850 is out of the shutter 822.

In step 950, the sample bed 850 moves along the transferring railway 860 toward the micro PET scanner 840 until the bed 850 arrives within the micro PET scanner 840. The micro PET scanner 840 starts to detect gamma rays from the same sample's parts as the micro MRI scanner 810 did. When the micro PET scanner 840 obtains sufficient data, it transmits the data to the imaging processor 870.

In step 960, the imaging processor 870 reconstructs the MRI image and the PET image, and fuses them by using data obtained from the two, that is, micro MRI scanner 810 and the micro PET scanner 840, respectively.

While the present invention has been shown and described with respect to particular embodiments, it will be apparent to those skilled in the art that many changes and modifications may be made without departing from the spirit and scope of the invention as defined in the appended claims.

What is claimed is:

1. An imaging apparatus for providing anatomical, hemodynamical, molecular and functional information on a subject, the imaging apparatus comprising:
    a magnetic resonance imaging scanner configured to obtain said anatomical information as well as hemodynamical information on said subject in an integrated form, said magnetic resonance imaging scanner generating magnetic fields external to said magnetic resonance imaging scanner, said magnetic resonance imaging scanner vulnerable to external RF signals whereby the magnetic resonance imaging scanner fails to correctly obtain anatomical information;
    a PET scanner configured to obtain said molecular and functional information, said PET scanner disposed in close proximity to the first scanner, said PET scanner vulnerable to magnetic fields generated by said magnetic resonance imaging scanner whereby the PET scanner is damaged by said magnetic fields generated by said magnetic resonance imaging scanner;
    an RF and magnetic shield enclosing a first predetermined space including said magnetic resonance imaging scanner but not the PET scanner, the RF and magnetic shield inhibiting external RF fields sufficiently that the magnetic resonance imaging scanner does not fail to correctly obtain anatomical information caused by said external RF fields, and preventing magnetic fields of said magnetic resonance imaging scanner from leaking outside the first predetermined space, a first opening defined in the RF and magnetic shield, the first opening selectively closable with a first shutter;
    a magnetic shield enclosing a second predetermined space including said PET scanner but not the magnetic resonance image scanner, and shielding the PET scanner from said magnetic fields out of said magnetic resonance imaging scanner, whereby the RF and magnetic shield enclosing the first predetermined space and the magnetic shield enclosing the second predetermined space together providing provide sufficient shielding such that the PET scanner is not reached by the magnetic fields generated by said magnetic resonance imaging scanner, a second opening defined in the magnetic shield enclosing the second predetermined space, the second opening selectively closable with a second shutter;
    an imaging processor configured to construct a fused image by processing anatomical and hemodynamical information obtained by the magnetic resonance imaging scanner, and molecular and functional information obtained by the PET scanner;
    a transferring railway system oriented in a substantially horizontal plane and extending between the magnetic resonance imaging scanner and the PET scanner through the first opening and the second opening, the railway system including a selectively rotatable portion;
    a bed movable along said transferring railway and for supporting said subject; and
    a controller coupled to the bed, the first shutter, and the second shutter, configured to control the movement of the bed along the railway, and coordinating the opening and closing of the first shutter and the second shutter so as to enable transfer of the subject on the railway between the magnetic resonance imaging scanner and the PET scanner while preventing magnetic field leakage from the magnetic resonance imaging scanner from reaching the PET scanner through the first opening and second opening.

2. The imaging apparatus of claim 1, wherein said transferring railway is sufficiently rigid and accurate to maintain coordinates for said subject between said magnetic resonance imaging scanner and the PET scanner.

3. The imaging apparatus of claim 2, wherein said magnetic resonance imaging scanner and the PET scanner each comprises a laser-guided calibration means for maintaining coordinates for said subject.

4. The imaging apparatus of claim 1, wherein said magnetic resonance imaging scanner is a UHF-MRI scanner, and said PET scanner is an HRRT-PET scanner.

5. The imaging apparatus of claim 1, the selectively rotatable portion being placed between said RF and magnetic shield enclosing the first predetermined space and said magnetic shield enclosing the second predetermined space.

6. The imaging apparatus of claim 1, further comprising a computer-readable recording medium, storing a program comprising instructions for a computer to operate the apparatus.

7. The imaging apparatus of claim 1, further comprising a computer-readable recording medium, storing a program comprising instructions for a computer to perform mathematical and computer techniques necessary to fuse anatomical and hemodynamical information, and molecular and functional information which are obtained by the apparatus.

8. A method of combining anatomical and hemodynamical information from an MRI scanner and molecular and functional information from a PET scanner on a test subject, the method comprising the steps of:
    disposing the MRI scanner and the PET scanner in close proximity to each other;
    surrounding the MRI scanner with an RF and magnetic shield to inhibit an external RF field from reaching the MRI scanner and to attenuate magnetic fields emanating from the MRI scanner, the RF and magnetic shield defining a first opening therein to enable transfer of the test subject therethrough, the RF and magnetic shield further including a first shutter for closing the opening, the first shutter selectively shiftable between a first closed position wherein the first shutter closes the first opening to complete the RF and magnetic shield and a second open position wherein the first opening is clear to enable transfer of the test subject;

surrounding the PET scanner with a magnetic shield for attenuating external magnetic fields to prevent damage to the PET scanner, the level of magnetic shielding provided by the RF and magnetic shield and the magnetic shield sufficient so that the magnetic fields emanating from the MRI scanner do not reach the PET scanner, the magnetic shield defining a second opening therein to enable transfer of a test subject therethrough, the magnetic shield further including a second shutter for closing the opening, the second shutter selectively shiftable between a first closed position wherein the second shutter closes the second opening to complete the magnetic shield and a second open position wherein the second opening is clear to enable transfer of the test subject;

disposing a transferring railway system in a substantially horizontal plane, the railway system extending between the MRI scanner and the PET scanner through the first opening and the second opening, the railway system including a bed for receiving the test subject, the bed selectively shiftable along the railway system;

using the MRI scanner to make a first image of a portion of the test subject;

using the PET scanner to make a separate second image of the portion of the test subject; and combining the first image and the second image to create a fused image of the portion of the test subject.

9. The method of claim 8, further comprising operably coupling a controller to the railway system, the first shutter, the second shutter, the MRI scanner, and the PET scanner, to automatically shift the bed between the MRI scanner and the PET scanner, and to synchronize shifting of the first shutter and the second shutter such that the magnetic fields emanating the MRI scanner do not reach the PET scanner when the bed is shifted along the railway system.

10. The method of claim 8, further comprising opening the first shutter, shifting the bed through the first opening, closing the first shutter, opening the second shutter, shifting the bed through the second opening, and closing the second shutter.

11. The method of claim 8, further comprising disposing a portion of the railway on a selectively rotatable structure positioned between the RF and magnetic shield and the magnetic shield, the selectively rotatable structure being operable to shift an orientation of the bed when the bed is disposed on the portion of the railway on the selectively rotatable structure.

12. The method of claim 11, further comprising opening the first shutter, shifting the bed through the first opening, closing the first shutter, reorienting the bed with the selectively rotatable structure, opening the second shutter, shifting the bed through the second opening, and closing the second shutter.

* * * * *